US00PP29969P2

(12) United States Plant Patent
Yanny

(10) Patent No.: US PP29,969 P2
(45) Date of Patent: Dec. 11, 2018

(54) ***CARPINUS* PLANT NAMED 'JN SELECT A'**

(50) Latin Name: *Carpinus caroliniana*
Varietal Denomination: JN Select A

(71) Applicant: JN Plant Selections, LLC, Milwaukee, WI (US)

(72) Inventor: Michael D. Yanny, Milwaukee, WI (US)

(73) Assignee: JN PLANT SELECTIONS, LLC, Milwaukee, WI (US)

( * ) Notice: Subject to any disclaimer, the term of this patent is extended or adjusted under 35 U.S.C. 154(b) by 34 days.

(21) Appl. No.: 15/530,156

(22) Filed: Dec. 7, 2016

(51) Int. Cl.
*A01H 5/00* (2018.01)

(52) U.S. Cl.
USPC ..... Plt./226

(58) Field of Classification Search
USPC ..... Plt./263.1, 226
See application file for complete search history.

*Primary Examiner* — Keith O. Robinson
(74) *Attorney, Agent, or Firm* — Penny J Aguirre

(57) ABSTRACT

A new cultivar of *Carpinus* plant named 'JN Select A' that is characterized by its foliage that consistently turns deep orange-red in color in the fall in Southern Wisconsin, its vigorous growth rate, and its good cold hardiness in Southern Wisconsin.

2 Drawing Sheets

Genus/species: *Carpinus caroliniana.*
Varietal denomination: 'JN Select A'.

BACKGROUND OF THE INVENTION

The present invention relates to a new and distinct cultivar of *Carpinus caroliniana* and will be referred to hereafter by its cultivar name, 'JN Select A'. 'JN Select A' represents a new cultivar of American hornbeam, ironwood, or musclewood, a deciduous tree grown for landscape use.

The Inventor discovered the new cultivar in May of 2003 as a chance seedling that was growing in a block of seedlings planted in 1996 from seed derived from open pollination of unnamed and unpatented plants of *Carpinus caroliniana* in Menomonee Falls, Wis. Both the female and male parent are unknown.

Asexual propagation of the new cultivar was first accomplished in 2004 by side-veneer grafting onto seedling *Carpinus caroliniana* understock by the Inventor in Menomonee Falls, Wis. Asexual propagation by side-veneer grafting and cleft grafting has determined that the characteristics of the new cultivar are stable and are reproduced true to type in successive generations.

SUMMARY OF THE INVENTION

The following traits have been repeatedly observed and represent the characteristics of the new *Carpinus*. These attributes in combination distinguish 'JN Select A' as unique and distinct cultivar of *Carpinus*.

1. 'JN Select A' exhibits foliage that consistently turns deep orange-red in color in the fall in Southern Wisconsin.
2. 'JN Select A' exhibits a vigorous growth rate.
3. 'JN Select A' exhibits good cold hardiness in Southern Wisconsin.

Typical plants of *Carpinus caroliniana* differ from 'JN Select A' in being less winter hardy, in having a less vigorous growth habit, and in having fall color that is less red in color.

'JN Select A' can be most closely compared to the *Carpinus caroliniana* cultivar 'JFS-KW6' (not patented)'. 'JFS-KW6' is similar to 'JN Select A' in having orange-red fall color in Southern Wisconsin. 'JFS-KW6' differs from 'JN Select A' in having a much less consistent orange-red fall foliage color and in showing a high degree of winter damage (twig die-back) in severe winters in Southern Wisconsin.

BRIEF DESCRIPTION OF THE DRAWINGS

The accompanying photographs were taken of 10 year-old plants of 'JN Select A' as grown in a trial garden in Menomonee Falls, Wis.

The photograph in FIG. 1 provides a side view of the plant habit and fall foliage of 'JN Select A'.

Figure 1:
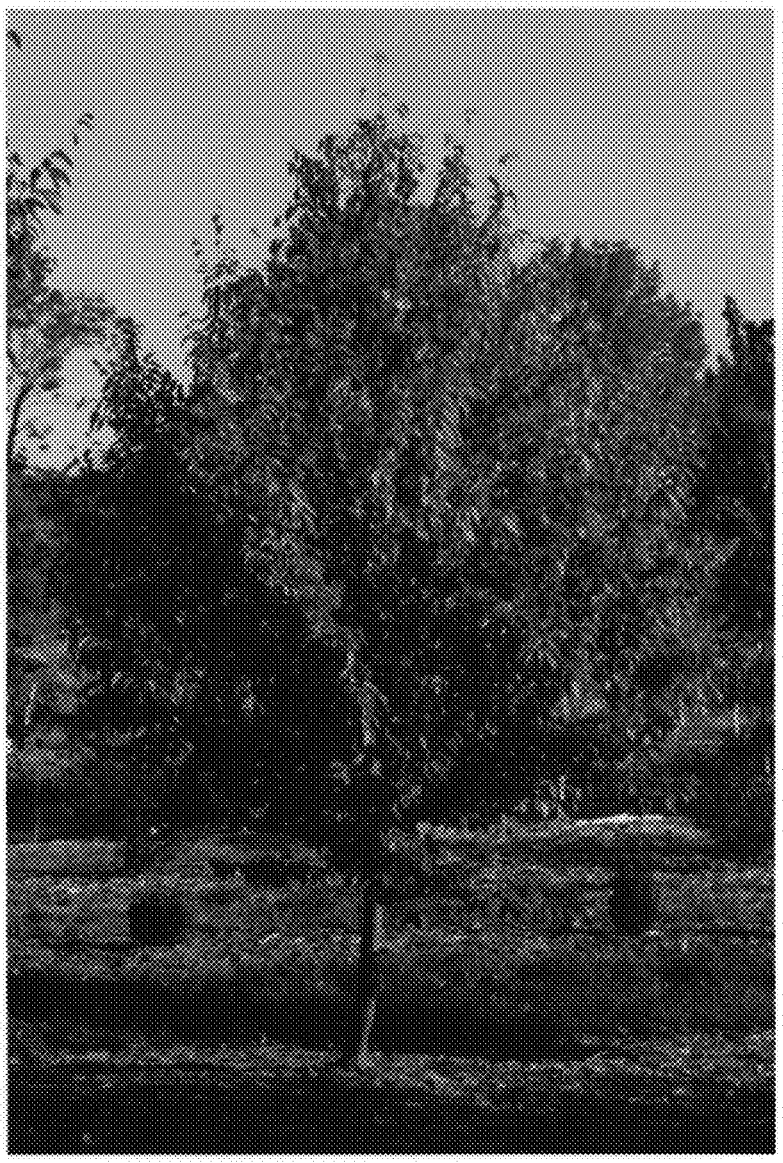
Figure 2:
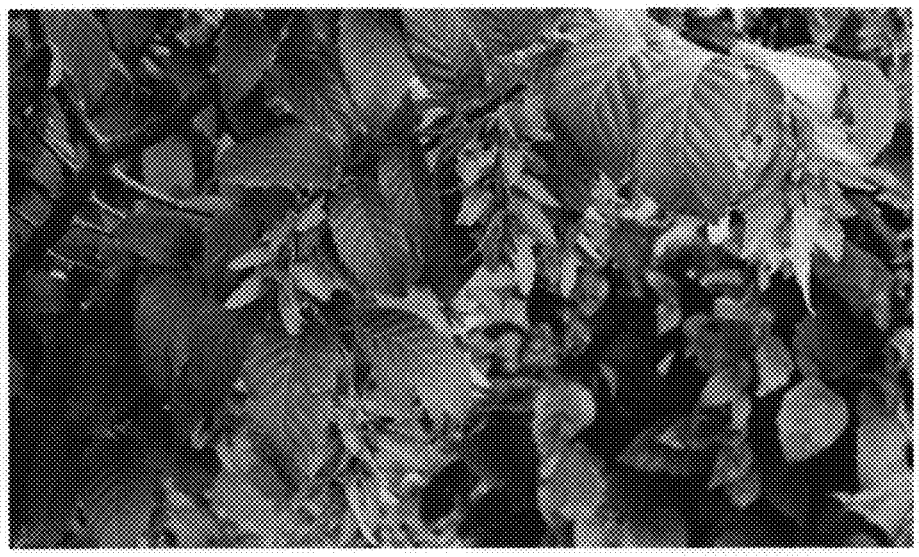

The photograph in FIG. 2 provides a close-up view of the fruit clusters and bracts of 'JN Select A'.

Figure 3:
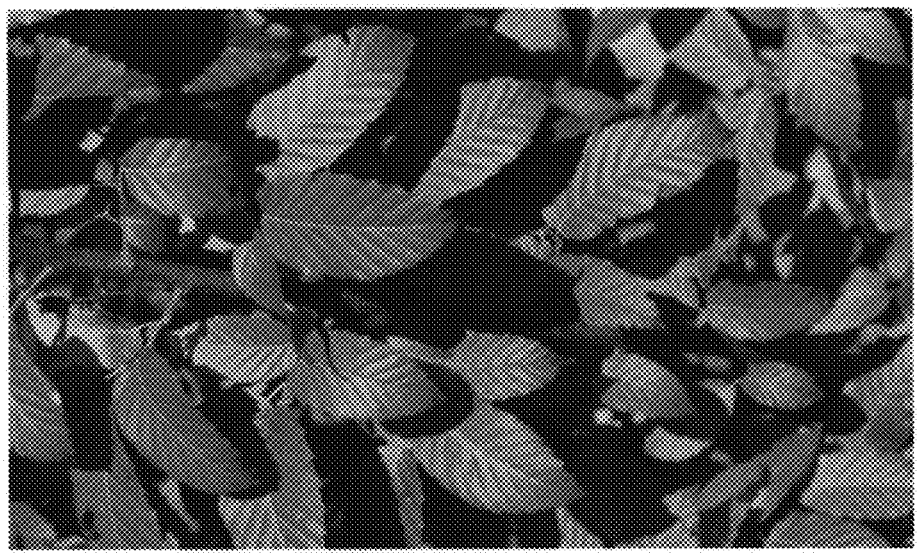

The photograph in FIG. 3 provides a close-up view of the fall foliage of 'JN Select A'.

The colors in the photographs are as close as possible with the digital photography and printing techniques utilized and the color codes in the detailed botanical description accurately describe the colors of the new *Carpinus*.

BOTANICAL DESCRIPTION OF THE PLANT

The following is a detailed description of 3 year-old plants as grown outdoors in 3-gallon containers and 10 year-old plants as grown in a trial garden in Menomonee Falls, Wis. Phenotypic differences may be observed with variations in environmental, climatic, and cultural conditions. The color determination is in accordance with The 2015 R.H.S. Colour Chart of The Royal Horticultural Society, London, England, except where general color terms of ordinary dictionary significance are used.

General description:

*Plant type*.—Deciduous tree.

*Plant habit*.—Upright and ovate in shape.

*Height and spread*.—Young tree 4-months in age; an average of 120 cm in height and 30 cm in spread.

*Hardiness*.—At least to U.S.D.A. Zone 4b to 7a with very little twig die-back observed due to winter in Southern Wisconsin.

*Diseases and pests*.—No susceptibility or resistance to diseases or pests has been observed to date.

*Growth rate*.—More vigorous than is typical for plants of *Carpinus caroliniana*.

*Propagation*.—Side-veneer grafting in mid to late July in a poly greenhouse under mist or cleft grafting in February with use of a hot callus pipe.

*Root development*.—A young plant is produced in about 1 year by side veneer grafting onto a 2-gallon containerized *Carpinus* seedling. Grafts are cut back in the spring and up shifted to produce a 2 to 3 ft. fully rooted plant in a 2-gallon container.

Branch description:

*Trunk size*.—An average of 10 cm in diameter measured 19 cm from soil line, 70 cm in height.

*Branch color*.—New growth (shoots) 200B, mature wood 201A, trunk; 177A.

*Branch shape*.—Rounded.

*Branch size*.—Lateral branches; an average of 3 mm in diameter and 23 cm in length, secondary branches; an average of 15 cm in length and 3 mm in diameter.

*Trunk texture*.—Dull and muscle-like, lenticels; moderate to densely covering the surface, linear in shape, 158A in color, up to 3 mm in with and 1 mm in height, an average of 25 lenticels per square cm.

*Branch surface*.—New growth; glabrous, shiny and lenticillate, old growth twigs; glabrous, dull and lenticillate, mature bark; dull and muscle-like, lenticels; moderate to densely covering the surface, lenticels on young stems are round in shape, lenticels on mature stems are linear in shape, 158A in color, up to 3 mm in width and 1 mm in height, an average of 25 lenticels per square cm.

*Branching*.—Alternately branched; lateral branch angles are almost horizontal to 60° from main stem (90° vertical), an average of lateral branches and 12 secondary branches per lateral branch.

*Leaf buds*.—An average of 5 mm in length and 2 mm in width, conical in shape, imbricate, 200B in color, puberulent surface.

*Stipules*.—None present.

Foliage description:

*Leaf shape*.—Oval-oblong.

*Leaf division*.—Simple.

*Leaf base*.—Rounded and slightly cordate.

*Leaf apex*.—Acuminate.

*Leaf venation*.—Pinnate, color; upper surface matches leaf color with very narrow midrib a color between 145B and I62B, lower surface 145B.

*Leaf margin*.—Biserrate.

*Leaf attachment*.—Petiolate.

*Leaf arrangement*.—Alternate.

*Leaf surface*.—Glabrous and smooth on upper and lower surfaces, lower surface has pubescence on veins.

*Leaf size*.—Up to 8.5 cm in length and 3.3 cm in width.

*Leaf internode length*.—An average of 2.5 cm.

*Leaf color*.—Upper surface 146A and lower surface 146B, fall upper surface; transition from 183A to 178A on outer leaves with some inner leaves a blend between 13A and 42B, fall lower surface 163C.

*Petioles*.—An average of 8.5 cm in length and 1 mm in width, rounded in shape, 162B in color, surface pubescent and smooth.

Flower description:

*Blooming period*.—Late April to early May in Southern Wisconsin.

*Inflorescence*.—Monoecious, cylindrical male and female catkins.

*Catkins*.—Penduolous and cylindrical in shape, male; an average of 3 cm in length and 6 mm in diameter, scales; average of 30, an average 3 mm in length and width, apex; cuspidate, base; truncate, a blend of 138A and 79B, an average of 6 stamens per bract, stamens 200A in color, pollen very scarce in quantity and 175A in color, female; an average of 1.1 cm in length and 4 mm in diameter, an average of 7 flowers with campanulate bracts 144A in color, 2 stigmas protruding about 1 mm and 70A in color.

*Flower fragrance*.—None.

*Flower lastingness*.—Female and male catkins present in spring, male not persistent.

*Peduncles*.—An average of 1.25 cm in length (from base of cluster to first leaves) and 1 mm in diameter, 200B in color, glabrous surface, moderately strong.

*Pedicels*.—None, sessile.

*Fruit and seed*.—Ribbed nutlet borne at the base of 3-lobed bracts and arranged in spike-like clusters, nutlet; 16 to 20 seeds per cluster, an average of 5 mm in length and 3.5 mm in width, 143C in color, ovate in shape, seed; 1 per nutlet, 1 mm in length and 1.5 mm in width, 165A in color, fruit clusters; an average of 5.5 cm in length and 3.7 cm in width, bracts; tri-lobed, apex acute, margins serrate, base rounded, an average of 2 cm in length and 1.35 cm in width, glabrous on both surfaces, 161B in summer and turning to 34B in fall with color turning color before foliage.

It is claimed:

1. A new and distinct cultivar of *Carpinus* plant named 'JN Select A' substantially as herein illustrated and described.

* * * * *